United States Patent
Fuenzalida Diaz et al.

(10) Patent No.: US 8,791,281 B2
(45) Date of Patent: Jul. 29, 2014

(54) METHOD FOR THE PRODUCTION OF LIGNOCERIC ACID

(75) Inventors: Miguel Angel Fuenzalida Diaz, Las Condes (CL); Alejandro Markovits Rojas, Las Condes (CL); Miriam Berrios Cornejo, Quilcura (CL); Mabel Keller Mena, Valparaiso (CL); Jose Rodrigo Vergara Salinas, Valsparaiso (CL); Glenda Cea Barcia, Valparaiso (CL); Andres Illanes Frontaura, Valparaiso (CL); Rolando Arturo Chamy Maggi, Valparaiso (CL); Andres Markovits Schersl, Valparaiso (CL); Araceli Olivares Miralles, Valparaiso (CL); Nadia Veronica Guajardo Ramirez, Valparaiso (CL)

(73) Assignee: Pontificia Universidad Catolica de Valparaiso, Valparaiso (CL)

( * ) Notice: Subject to any disclaimer, the term of this patent is extended or adjusted under 35 U.S.C. 154(b) by 424 days.

(21) Appl. No.: 13/320,187

(22) PCT Filed: May 10, 2010

(86) PCT No.: PCT/IB2010/052057
§ 371 (c)(1), (2), (4) Date: Feb. 6, 2012

(87) PCT Pub. No.: WO2010/131186
PCT Pub. Date: Nov. 18, 2010

(65) Prior Publication Data
US 2012/0130100 A1  May 24, 2012

(30) Foreign Application Priority Data

May 13, 2009  (CL) .................................. 1167-2009

(51) Int. Cl.
*C07B 33/00* (2006.01)
*C11B 3/06* (2006.01)

(52) U.S. Cl.
USPC ............ 554/138; 554/195; 554/132; 554/124

(58) Field of Classification Search
None
See application file for complete search history.

(56) References Cited

U.S. PATENT DOCUMENTS 2,519,903 A * 8/1950 Hasselstrom ................. 530/208
2,880,216 A * 3/1959 Burgon et al. ................ 552/545

* cited by examiner

Primary Examiner — Yate K Cutliff
(74) Attorney, Agent, or Firm — Merchant & Gould P.C.

(57) ABSTRACT

The invention is related to a process for production of lignoceric acid from mixtures of long-chain aliphatic alcohols that contain lignoceric alcohol, wherein the process consists in oxidizing the mixture in a biphasic catalytic system using quaternary ammonium peroxotungstophosphate as a catalyst and hydrogen peroxide as an oxidant, followed by several physical or chemical unitary steps to separate and purify the lignoceric acid.

16 Claims, 1 Drawing Sheet

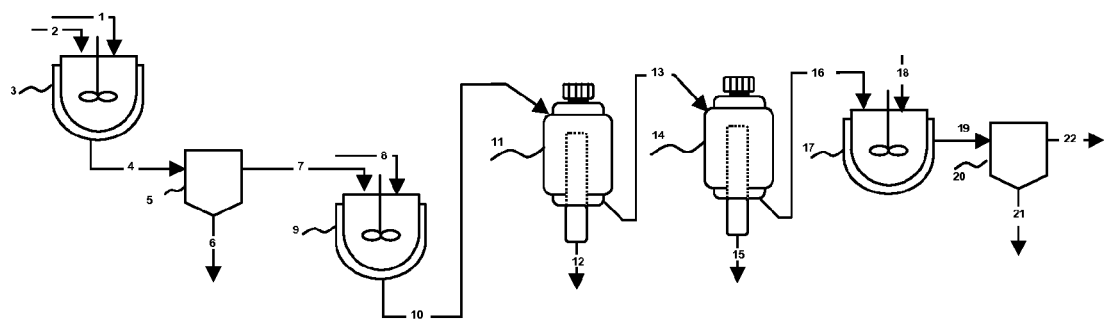

METHOD FOR THE PRODUCTION OF LIGNOCERIC ACID

This application is a National Stage Application of PCT/IB2010/052057, filed 10 May 2010, which claims benefit of Ser. No. 1167-2009, filed 13 May 2009 in Spain and which applications are incorporated herein by reference. To the extent appropriate, a claim of priority is made to each of the above disclosed applications.

The present invention is related to a process to obtain lignoceric acid from lignoceric alcohol.

BACKGROUND OF THE INVENTION

Recent research at the U.S. Department of Agriculture (www.hbci.com/~wenonah/new/pnutskin.htm) have brought attention into the potential use of lignoceric acid as an ingredient in dermal oils and creams and hair conditioners, due to its excellent properties as a moisturizing and softening agent when used in said products. Currently, behenic acid is used for the same functions and is commercially available, which is not the case for lignoceric acid. Researchers consider that a mixture of both fatty acids could have higher moisturizing properties than those of behenic acid alone. The USDA researcher's interest arose from the discovery of the presence of both behenic acid and lignoceric acid in the thin skin that coats peanut seeds, which they consider could become a potential source for the commercial production of lignoceric acid, currently inexistent.

In fact, lignoceric acid is only found in trace amounts in the majority of the vegetable oils, with the exception of peanut oil (1%). It is contained in higher amounts in sources with no commercial production, such as oil from the seeds of the red sandalwood tree (*Adenanthera pavonina*), a leguminous tree (up to 25%), or in commercially available sources that are very valuable by themselves and do not warrant their processing to obtain lignoceric acid, such as e.g. carnauba wax (30%) and rice bran wax (40%). A potential source that could be eventually used for production of lignoceric acid is the thin skin that coats peanut seeds, as mentioned before.

Currently, no process is known to recover lignoceric acid at a commercial scale from any of the previously mentioned sources for the purpose of application in large scale products and no providers are available, excepting companies selling laboratory analyticals or fine chemicals, such as e.g. Sigma Chemicals, US$ 515/10 g (99%).

Another possible commercial source of lignoceric acid is black liquor soaps. These are residues of the sulfate process or Kraft pulping of pine wood for the production of cellulose and fundamentally comprise sodium salts of fatty acids, among them lignoceric acid, salts of rosin acids, a complex series of non-saponifiable materials and dark degradation products such as lignin. The solid content of black liquor soaps ranges from 40 to 70% by weight. The black liquor is acidified with sulfuric acid to convert it into "tall oil", which is used as a source for obtaining fatty acids and distilled rosin acids used in the manufacture of esters, alkidic resins and the like. Since the color of tall oil influences the quality of the obtained products, several processes have been developed for their refining, i.e. for removing compounds responsible for the color of tall oil.

One of the earliest of such color removing processes is disclosed in the U.S. Pat. No. 2,519,903, filed on Aug. 22, 1950 and entitled "Removal of the sodium salt of lignoceric acid and other materials from a tall oil soap". The disclosed process essentially consists in diluting black liquor soaps with water to a solid content ranging from 0.5 to 25% in weight, and letting the dilution to settle during at least one hour. A large part of the colored compounds are among the decanted solids, together with the sodium salt of lignoceric acid, or sodium lignocerate. Although only the refining process is claimed, processes for recovering lignoceric acid, which can amount up to 1.4% by weight of the solids in the black liquor according to the authors, are also disclosed.

However, the disclosed refining process has never been implemented commercially, partly due to the costs associated to the large dilution of the solids, high energy consumption for the recovery of sodium sulfate through evaporation of large volumes of water, and finally the development of better and more efficient processes for the refining of tall oil. Nevertheless, in view of the objectives of the present invention, the process disclosed in the U.S. Pat. No. 2,519,903 constitutes the closest prior art to the present invention, as far as there are no other processes in the state of art for the production of lignoceric acid for large scale applications.

The objective of the present invention is to provide a novel process for the production of lignoceric acid, which is easy to implement at a commercial scale and is able to produce lignoceric acid at a cost compatible for bulk utilization and application in large scale products such as cosmetic creams and lotions and the like.

The process of the invention that is described in the following paragraphs is illustrated by nine examples and one figure (FIG. 1) and fulfills the abovementioned objective. It consists of a catalytic oxidation step of a raw material that comprises lignoceric alcohol, followed by a series of other physical and chemical steps that interact synergistically between them to yield lignoceric acid. The entire process as well as each of its steps has been developed or adapted according to the nature of the raw material, intermediate products and the final product, and constitutes an invention with no antecedents in the state of the art, which is also not obvious for someone skilled in the art. For the purpose of this invention, the raw material can be a material composition with a content of at least 50% by weight of lignoceric alcohol, and the process of the invention comprises eight chemical and physical steps consisting of:

a) forming a reactant mixture by contacting the raw material, quaternary ammonium peroxotunsgtophosphate and an aqueous solution of hydrogen peroxide during a time interval sufficient to form a reacted mixture comprising lignoceric acid;

b) separating the reacted mixture from step (a) into an aqueous phase and an organic phase, wherein the organic phase comprises lignoceric acid;

c) forming a saponifying mixture by contacting the organic phase from step (b) with an aqueous solution of one or more alkaline metal hydroxides, where the alkaline metal hydroxides can be selected from the group consisting of sodium hydroxide or potassium hydroxide, heating the mixture to a temperature of at least 90° C. and keeping said temperature during a time interval sufficient to form a saponified mixture comprising the lignocerate;

d) evaporating the saponified mixture from step (c) to obtain a residue comprising the lignocerate, wherein said residue has a water content of at most 1% by weight based on the total residue weight;

e) distilling the residue from step (d) at a temperature ranging from 200° C. to 350° C. and at a pressure of less than 60 mbar to obtain a distillate and a solid residue, wherein the residue comprises the lignocerate;

f) forming a mixture by contacting the solid residue from step (e) with an aqueous solution containing one or more acids selected from the group consisting of acetic acid, hydrochloric acid and sulfuric acid, heating the residue and the solution mixture up to a temperature between 90° C. and 150° C. during a time interval sufficient to form a liquid mixture comprising lignoceric acid;

g) cooling the liquid mixture from step (f) down to at least room temperature or less, and keeping said temperature during a time interval sufficient to form a liquid phase and a solid phase, wherein the solid phase comprises the lignoceric acid; and h) separating the solid phase from step (g) from the liquid phase, wherein the solid phase comprises the lignoceric acid.

Lignoceric alcohol or tetracosanol is a convenient raw material, since it is relatively abundant in many readily available sources, such as some plant waxes, e.g. sugar cane wax, aliphatic alcohols derived from tall oil or mixtures of industrial synthetic fatty alcohols obtained through oxidation of paraffins. All of these are abundant and convenient sources to obtain lignoceric alcohol.

DETAILED DESCRIPTION OF THE PROCESS

The raw material with a content of at least 50% by weight of lignoceric alcohol is oxidized in a biphasic liquid system using a quaternary ammonium peroxotungstophosphate as a phase transfer catalyst and aqueous hydrogen peroxide as an oxygen donor. To this end, a reactant mixture is formed by contacting the liquid raw material, quaternary ammonium peroxotunsgtophosphate and an aqueous solution of hydrogen peroxide during a time interval sufficient to form a reacted mixture comprising lignoceric acid.

The reaction is carried out in a solvent free system at temperatures ranging from 90° C. to 120° C. The reaction can be carried out in stirred batch reactors, stirred fed-batch reactors with programmed addition of hydrogen peroxide or in continuous stirred tank reactors, with one flow inlet formed by a mixture of raw material and catalyst and another flow inlet conveying the hydrogen peroxide aqueous solution.

The phase transfer catalyst can be prepared using either a quaternary ammonium salt or a mixture of different quaternary ammonium salts and phosphotungstic acid as illustrated in Example 1. All the ingredients for this preparation are commercially available. In the reactant mixture, the mass of raw material can be 20 to 300 higher than the mass of catalyst.

For the oxidation, different oxidants can be used, including potassium dichromate, potassium permanganate, sodium periodate, peracetic acid, potassium chlorate, or potassium perchlorate, but the preferred oxidant is hydrogen peroxide. The present invention can use a hydrogen peroxide aqueous solution with any given concentration, but it is more convenient to use hydrogen peroxide with a concentration of 30% by weight or higher, preferably 50% by weight. The mass of aqueous solution of hydrogen peroxide used for the oxidation can be up to six times the stoichiometric amount required to oxidize all the lignoceric alcohol in the reacting mixture to lignoceric acid. Numerous quaternary ammonium salts or mixtures of two or more of such salts can be used to prepare the catalyst, such as: tetrabutyl ammonium bromide, tetrabutyl ammonium hydrosulfate, benzyl triethyl ammonium chloride, tetraethyl ammonium bromide, tetraethyl ammonium hydroxide, tetramethyl ammonium hydroxide, phenyl trimethyl ammonium chloride methyl trioctyl ammonium chloride, tricapryl methyl ammonium chloride and the like. Nevertheless, for the purpose of the present invention it is preferably used a mixture of methyl trioctyl ammonium chloride and tricapryl methyl ammonium chloride with larger amounts of the former, which is commercially available under the trademark Aliquat 336, manufactured by Cognis.

Under the reaction conditions disclosed in the present invention, the oxidation yield of lignoceric alcohol to lignoceric acid is surprisingly high in comparison with the oxidation yields of lower alcohols known in the state of art, as shown in Example 2. Hence, the oxidation of eicosanol with hydrogen peroxide in the presence of tricapryl methyl ammonium peroxotungstophosphate catalyst immobilized on a molecular sieve of titanium zeolite (Ti-MCM-41) had a maximum yield of 53% and a conversion of 70% (Qiubin Kan et al. "Catalytic oxidation a-eicosanol into eicosanoic acid in the presence of Ti-MCM-41 or active component supported catalyst" Microporous and Mesoporous Materials 44-45: 609-617, 2001), or a maximum yield of 50.8% and a conversion of 80.2% (Bi Ying-li et al. "Oxidation of long chain primary alcohols to acids over the quaternary ammonium peroxotungstophosphate catalyst system" React. Kinet. Catal. Lett. 72(1): 73-82, 2001), whereas the maximum yield for the oxidation of lignoceric alcohol to lignoceric acid in the present invention was 78.1% and the conversion was 93.4%, indicating that in addition to a higher yield the catalytic system of the present invention also exhibits a surprisingly high selectivity toward lignoceric alcohol. The reaction course can be monitored by measuring the decrease of lignoceric alcohol concentration in the reacted mixture or the appearance and concentration increase of lignoceric acid in the reacting mixture, or both. The measurement of both lignoceric alcohol concentration decrease and lignoceric acid appearance and concentration increase in the reacted mixture are performed by gas chromatography as described in Example 2.

Once the reaction mixture has achieved a certain content of lignoceric acid, the organic phase of the mixture is separated from the aqueous phase resulting from the hydrogen peroxide decomposition. This can be done by decanting the reacted liquid mixture and separating the aqueous phase through the bottom of the decanter, by centrifugation, and also can be conveniently done by cooling down the reacted mixture to room temperature, which solidifies the organic phase and allows an easier removal of the aqueous phase through the bottom of the decanter. Even more preferably, when the reaction is performed in stirred batch reactors or stirred fed-batch reactors, a discharge valve can be provided at the bottom of the reactor to facilitate the phase separation operation.

The separated organic phase is contacted with an aqueous solution of sodium hydroxide or potassium hydroxide or an aqueous solution containing both sodium and potassium hydroxide, wherein the concentration of the hydroxide or hydroxides ranges from 40% to 50% by weight of the aqueous solution to form a saponifying mixture that is heated to a temperature of at least 90° C. during an time interval sufficient to form a saponified mixture comprising lignocerate. The most convenient way to detect the formation of a saponified mixture consists in measuring the decrease of alkalinity or hydroxide concentration as shown in Example 3. When the saponifying mixture is heated to 130° C. for a maximum of 15 minutes with a 10% or less stoichiometric excess of hydroxide with respect to the lignoceric acid in the saponifying mixture, it has been found that the saponification is complete.

The saponified mixture is then fed to a falling film evaporator or a short-path distiller wherein the heated surface temperature ranges from 150 to 300° C. and the pressure inside the evaporator or the short-path distiller is lower than the atmospheric pressure, to obtain a residue comprising the lignocerate and at most 1% by weight of water.

The residue is then distilled, preferably in a short-path distiller, wherein the heated surface temperature ranges from 200° C. to 400° C., preferably 250° C., and the pressure is less than 1 mbar, to obtain a second residue comprising sodium or potassium lignocerate or a mixture of both.

The second residue comprising lignocerate is contacted with an aqueous solution containing one or more acids selected from the group consisting of acetic acid, hydrochloric acid and sulfuric acid, and the residue and the solution mixture are heated up to a temperature between 90° C. and 150° C. during a time interval sufficient to form a liquid mixture comprising lignoceric acid. During this step, the lignocerate is converted to lignoceric acid with a concomitant decrease in the amount of solid phase because the acid formed in this way has a melting point of 84° C., while lignocerate has a melting point of 250° C., so that all the lignocerate will be converted to lignoceric acid. The contacting of lignocerate and the acid or acid mixture can be conveniently carried out in a stirred tank provided with a reflux condenser, conveniently provided with a draining valve at the bottom and a conventional form of heat exchanger such as a heating jacket or coil through which a heat transfer fluid circulates.

Once all the lignocerate had been converted to lignoceric acid, the liquid mixture in the reactor is cooled down, usually to room temperature, causing the lignoceric acid, which is insoluble in aqueous medium, to solidify, thus allowing an easy separation of the solids from the liquid phase, preferably by filtering the mixture. Said off-white solid phase is a product generally suitable for many of the eventual applications of said acid.

However, if a better colored product is desired, the solid phase is then distilled, preferably in a short-path distiller, wherein the heated surface temperature ranges from 200° C. to 400° C., preferably a temperature higher than 300° C., and at a pressure less than 60 mbar, preferably 1 mbar or less, to obtain a whitish distillate comprising lignoceric acid.

Alternatively, if a better colored product is desired, the solid phase from the acidification reactor is contacted with one or more solvents selected from the group consisting of acetone, acetic acid, chloroform, toluene, xylene, ethanol, methanol, ethyl acetate, hexane, cyclohexane, butanol, dichloromethane, dimethylsulfoxide and water, and the resulting mixture is heated up to at least 90° C. during a time interval sufficient to dissolve or melt the solid phase. The contacting can be carried out by mixing the solid phase containing lignoceric acid with the solvent or solvent mixture in a stirred reactor. The heating can be carried out in a stirred reactor provided with a reflux condenser or also in a pressurized stirred reactor.

Once the solid phase has been dissolved and/or melted, it is cooled down to room temperature or less than room temperature if desired, which results in the formation of a whitish solid phase. Said whitish solid phase can be redistilled, preferably in a short-path distiller, with a heated surface temperature ranging from 200° C. to 400° C., preferably higher than 300° C., and at a pressure less than 60 mbar in the evaporation chamber, preferably 1 mbar, to obtain a white distillate comprising at least 80% by weight of lignoceric acid.

The following examples illustrate different aspects and practical embodiments of the process of the present invention, without excluding other embodiments that are evident from the present disclosure for someone averagely skilled in the art.

EXAMPLE 1

Preparation of the Catalyst 3 g of phosphotungstic acid (Sigma Chemicals) and 10 mL of an aqueous solution comprising 8% by weight of hydrogen peroxide were mixed in 250 mL flask and then 20 mL of water and 4 g of methyl triethyl ammonium chloride (Aliquat 336, Cognis) dissolved in 50 mL of dichloromethane were added. The mixture was stirred for 15 minutes on a magnetic stirrer and was subsequently poured into a decanting funnel to separate the aqueous phase from the organic phase. Once separated, the organic phase was dried over anhydrous sodium sulfate and the anhydrous organic phase was subsequently put into a Buchi rotary evaporator to remove the dichloromethane to yield about 7 grams of a viscous liquid, the quaternary ammonium peroxotungstophosphate catalyst.

EXAMPLE 2

Oxidation of the Raw Material 300 g of a raw material comprising 80% by weight of lignoceric alcohol and 20% of other aliphatic alcohols, mainly docosanol and hexacosanol (Alchemist International Ltd., Hong Kong) was loaded into a 2 L jacketed glass reactor Oka Eurostar) provided with a variable speed stirrer, a jacket to circulate heating fluid (Therminol 66 thermal oil) and a reflux condenser. The temperature of the heating fluid was 95° C., which kept the reactor temperature at 90° C. during the reaction. Once the raw material melted and reached 90° C., 6 g of the catalyst prepared as described in Example 1 and 72 mL of 50% by weight of hydrogen peroxide were added to the melted mixture to start the oxidation reaction. The reacting mixture was stirred at 200 rpm by the reactor propeller. After two reaction hours, an additional 72 ml of 50% by weight of hydrogen peroxide were added, repeating the addition of 72 mL 50% by weight hydrogen peroxide after six reaction hours. After eight reaction hours, stirring was stopped and the aqueous and organic phases were left to separate. A sample was taken from the organic phase for analysis, which indicated a conversion yield of 78.1% from lignoceric alcohol to lignoceric acid and a total lignoceric alcohol conversion of 93.4%, where the yield is calculated as the mass percentage of lignoceric alcohol oxidized to lignoceric acid and the conversion is calculated as the mass percentage of total lignoceric alcohol transformed (by oxidation or another reaction).

Sample Analysis

Lignoceric alcohol and lignoceric acid were determined using an HP 6890 gas chromatographer with autosampler, provided with a HP-5 column (30 m×0.25 mm of diameter× 0.25 μm) and a flame ionization detector operating in split mode (30:1). The injector temperature was set at 300° C. and the detector temperature was set at 320° C. The initial temperature of the column was 160° C. and was increased at a rate of 5° C./min, and keeping the isotherm for 10 minutes. The carrier gas was helium with constant flow (1 mL/min).

Derivatization of Samples for Analysis

Between 400 and 500 mg of sample are weighed in a scintillation vial with 20 to 30 mg of cholesterol as an internal standard. Subsequently, 15 mL of chloroform were added and the mixture was vortexed or sonicated if necessary to dissolve the components. 500 μL were transferred to a chromatography vial and evaporated under nitrogen. Then, 300 μL of sylanizing reactant (Bis(trimethyl)silyl trifluoroacetamide) and 400 μL of pyridine were added. The vial was closed and heated for 15 minutes, stirred again and 1.0 μL was injected into the chromatograph.

From the chromatographic report, peaks of lignoceric acid and lignoceric alcohol were identified by comparison to the retention times of corresponding standards. The lignoceric alcohol and lignoceric acid standards were purchased from Sigma (L 3507 and L 6641 respectively) with purities of 99% or more and weight percentages were calculated for each species.

EXAMPLE 3

Saponification of the Organic Phase 251 g of the organic phase from Example 1 were loaded into an Erlenmeyer flask provided with a reflux condenser and mixed with 40 g of 50% sodium hydroxide, subsequently keeping the mixture at the boiling point for 2 hours. Then, 1 g of the saponified mixture was suspended in 50 mL of distilled water and the free alkalinity of the sample was measured by titration in a Mettler Toledo DL-56 titrator, which was equivalent to 0.35 g of NaOH per gram of the saponified mixture.

EXAMPLE 4

Dehydration of the Saponified Mixture 258 g of the saponified mixture were loaded into the feeder of a KDL-5 short-path evaporator (UIC GmbH) and were kept at 95° C. The evaporator was operated at 250° C. and with a pressure of 700 mbar. The condenser temperature was 23° C. and the residue temperature was 250° C. The residue, once cooled down to room temperature, was a solid with a water content of 0.08% measured by the Karl Fischer titration method.

EXAMPLE 5

Molecular Distillation 223 g of the residue from Example 4 were crushed and loaded into the feeder of a KDL-5 short-path evaporator (UIC GmbH) and were kept at 250° C. until the product has completely melted. The evaporator was operated at 310° C. and with a pressure of 0.5 mbar. The condenser temperature was 75° C. and the residue temperature was 340° C. The residue was solid at room temperature.

1 g of the residue was suspended in 50 mL of water in a 250 mL Erlenmeyer flask and immediately 3 mL of concentrated hydrochloric acid were added. The pH value of the mixture was 2. The mixture was filtered to yield dark brown solids with a waxy appearance. The solids were dried and analyzed by gas chromatography as described in Example 3, which indicated a lignoceric acid content of 83.6% by weight of solid.

EXAMPLE 6

Acidification 126 g of the residue from Example 5 were suspended in water at 60° C. in an Erlenmeyer flask provided with a reflux condenser, then 40 mL of 50% sulfuric acid were added and the mixture was heated under reflux for 1 hour. The mixture was subsequently cooled down to 35° C. and the resulting solid-liquid dispersion was filtered through filter paper. The filtered solids were washed with water until neutral pH. The product was dried and analyzed by gas chromatography as described in Example 3. The analysis indicated a lignoceric acid content of 87.5% by weight of sample.

EXAMPLE 7

Short-path Distillation 58 g of the acidulated solid from Example 6 were loaded into the feeder of a KDL-5 short-path evaporator and were kept at 95° C. The evaporator was operated at 300° C. and with a pressure of 0.73 mmHg. The condenser temperature was 90° C. and the residue temperature was 300° C.

48 g of a whitish distillate were obtained. The distillate was analyzed by gas chromatography as described in Example 2, which determined a lignoceric acid content of 91.7% by weight of lignoceric acid in the distillate.

In Examples 4, 5 and 7, the feeding rates into the evaporator of the short-path unit were 0.37 L/h.

EXAMPLE 8

Solvent Refining 2 g of the acidulated solids from Example 6 were contacted with 100 g of toluene at 100° C. in an Erlenmeyer flask provided with a reflux condenser that was magnetically stirred for 1 hour. The flask was allowed to cool down to room temperature and the resulting solid-liquid suspension was washed with toluene and dried, yielding white solids with a waxy appearance. The solids were analyzed by gas chromatography as described in Example 2, which determined a lignoceric acid content of 92.1% by weight of lignoceric acid.

The suspension was filtered at 35° C., washed with toluene and dried. A white waxy mass with 92.1% of lignoceric acid was obtained.

DESCRIPTION OF THE DRAWINGS

FIG. 1 shows a scheme of the process. A stream 1 comprising an aqueous solution of hydrogen peroxide and a stream 2 comprising a mixture of raw material containing lignoceric alcohol and catalyst enters into the stirred reactor 3. The reacted mixture stream 4 leaving the reactor 3 enters into a separator 5. An aqueous phase stream 6 and an organic phase stream 7 leave the separator 5. The organic phase 7 and a stream 8 comprising an aqueous solution of sodium or potassium hydroxide enter to a stirred saponification reactor 9. The saponified mixture 10 leaving the saponification reactor 9 enters into the evaporator 11. An aqueous stream 12 and an evaporated stream 13 leave the evaporator 11. The evaporated stream 13 enters into a short-path distiller 14. A distillate stream 15 and a residue stream 16 leave the short-path distiller 14. The residue stream 16 and an aqueous acid solution 18 enter into an acidification reactor 17. The acidified stream 19 leaves the acidification reactor 17 and enters into a phase separator 20. An aqueous acid solution stream 22 and a solid lignoceric acid stream 21 leave the phase separator 20.

The invention claimed is:

1. A process to obtain lignoceric acid wherein the lignoceric acid is obtained from a raw material comprising at least 50% by weight of lignoceric alcohol by means of a process comprising the steps of:
   a) forming a reactant mixture by contacting the raw material, quaternary ammonium peroxotunsgtophosphate and an aqueous solution of hydrogen peroxide during a time interval sufficient to form a reacted mixture comprising lignoceric acid;

b) separating the reacted mixture from step (a) into an aqueous phase and an organic phase, wherein the organic phase comprises lignoceric acid;

c) forming a saponifying mixture by contacting the organic phase from step (b) with an aqueous solution of one or more alkaline metal hydroxides, where the alkaline metal hydroxides can be selected from the group consisting of sodium hydroxide or potassium hydroxide, heating the mixture to a temperature of at least 90° C. and keeping said temperature during a time interval sufficient to form a saponified mixture comprising the lignocerate;

d) evaporating the saponified mixture from step (c) to obtain a residue comprising the lignocerate, wherein said residue has a water content of at most 1% by weight based on the total residue weight;

e) distilling the residue from step (d) at a temperature ranging from 200° C. to 400° C. and at a pressure of less than 60 mbar to obtain a distillate and a second solid residue that comprises the lignocerate;

f) forming a mixture by contacting the second solid residue from step (e) with an aqueous solution comprising one or more acids selected from the group consisting of acetic acid, hydrochloric acid and sulfuric acid, heating the solid residue and the solution mixture up to a temperature between 90° C. and 150° C. and maintaining the temperature of the mixture during a time interval sufficient to form a liquid mixture;

g) cooling the liquid mixture from step (f) down to at least room temperature or less, and keeping said temperature during a time interval sufficient to form a liquid phase and a solid phase, wherein the solid phase comprises lignoceric acid; and h) separating the solid phase from step (g) from the liquid phase, wherein the solid phase comprises the lignoceric acid.

2. The process according to claim 1 wherein the temperature of the reacting mixture of step (a) ranges from 90° C. to 120° C.

3. The process according to claim 1 wherein in step (a) the mass ratio between lignoceric alcohol and quaternary ammonium peroxotungstophosphate ranges from 20:1 to 300:1

4. The process according to claim 1 wherein in step (a) the molar ratio between hydrogen peroxide and lignoceric alcohol ranges from 1:1 to 6:1

5. The process according to claim 1 wherein in step (a) the quaternary ammonium peroxotungstophosphate is a mixture of methyl trioctyl ammonium peroxotungstophosphate and tricapryl methyl ammonium peroxotungstophosphate.

6. The process according to claim 1 wherein in step (a) the aqueous solution of hydrogen peroxide comprises at least 30% by weight of hydrogen peroxide.

7. The process according to claim 1 wherein in step (c) the aqueous solution comprises between 40% and 50% by weight of an alkaline metal hydroxide and the temperature of the saponifying mixture is 130° C.

8. The process according to claim 1 wherein in step (d) the evaporation is carried out in a falling film evaporator and the heating surface temperature ranges from 150° C. to 300° C. and the pressure inside the evaporator chamber is at most the atmospheric pressure.

9. The process according to claim 1 wherein the distillation of step (e) is carried out in a short-path distiller and the heating surface temperature in the evaporator ranges from 200° C. to 400° C. and the pressure inside the evaporator chamber is less than 60 mbar.

10. The process according to claim 1 wherein the solid phase comprising lignoceric acid is distilled at a temperature ranging from 200° C. to 400° C. and at a pressure of less than 60 mbar to obtain a residue that comprises lignoceric acid.

11. The process according to claim 10 wherein the distillation is carried out in a short-path distiller and the heating surface temperature in the evaporator is at least 300° C. and the pressure inside the evaporator chamber is at most 1 mbar.

12. The process according to claim 1 wherein a mixture is formed by contacting the solid phase comprising lignoceric acid with one or more solvents selected from the group consisting of acetone, acetic acid, chloroform, toluene, xylene, ethanol, methanol, ethyl acetate, hexane, cyclohexane, butanol, dichloromethane, dimethylsulfoxide and water, and the mixture of the solid phase and the solvent or solvent mixture is heated up to at least 90° C. during a time interval sufficient to form a liquid mixture.

13. The process according to claim 12 wherein the liquid mixture is cooled down to at least room temperature or less and is kept cool at said temperature during a time interval sufficient to form a solid phase and a liquid phase.

14. The process according to claim 13 wherein the solid phase is separated from the liquid phase and the separated solid phase is distilled at a temperature ranging from 200° C. to 400° C. and at a pressure of less than 60 mbar to obtain a residue that comprises lignoceric acid.

15. The process according to claim 14 wherein the distillation is carried out in a short-path distiller and the heating surface temperature in the evaporator is at least 300° C. and the pressure inside the evaporator chamber is at most 1 mbar.

16. The process according to claim 15 wherein the residue comprises at least 80% by weight of lignoceric acid.

* * * * *